United States Patent
Reitberg

(10) Patent No.: US 6,224,897 B1
(45) Date of Patent: *May 1, 2001

(54) METHODS TO ABATE THE USE OF TOBACCO BY HUMANS

(75) Inventor: Donald Paul Reitberg, Bedminster, NJ (US)

(73) Assignee: Novartis Consumer Health S.A., Nyon (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/162,754

(22) Filed: Sep. 29, 1998

(51) Int. Cl.$^7$ .................................................. A61K 9/72
(52) U.S. Cl. ..................... 424/443; 424/444; 424/446; 424/449; 514/343; 514/813
(58) Field of Search .................................. 424/443–444, 424/446, 449, 484–488; 574/343, 812, 813

(56) References Cited

U.S. PATENT DOCUMENTS

| 5,055,478 | 10/1991 | Cooper et al. | 514/343 |
|---|---|---|---|
| 5,549,906 | 8/1996 | Santus | 424/440 |
| 5,596,007 | 1/1997 | Keenan et al. | 514/343 |

OTHER PUBLICATIONS

Goodman & Guzman 4th Edition, 1970.*
Richmond, R.L. et al., Addiction, vol. 92(1), 1997, pp. 27–31.
Yudkin, P.L. et al., British Journal of General Practice, Mar. 1996, pp. 145–148.
Cinciripini, P.M. et al., Journal of Consulting Clinical Psychology, vol. 64(2), pp. 314–323, 1996.
Swartz, S.H. et al., Journal of General Internal Medicine, vol. 10(2), Dec. 1995, pp. 656–662.
Smith, M.D. et al., American Pharmacy, vol. 8, Aug. 1995, pp. 20–9, 32.
Davis, Jr., L.J. et al., Journal of Clinical Psychology, vol. 50(6), Nov. 1994, pp. 918–930.
Richmon, R.L. et al., Medical Journal of Australia, vol. 161(2), Jul. 18, 1994, pp. 130–135.
Haxby, D.G., American Journal of Health–Syst Pharm, vol. 52(3), Feb. 1, 1995, pp. 265–81, 314–5.
Mankani, S.K. et al., Journal of Occupational Environmental Medicine, vol. 38(2), Feb. 1996, pp. 184–189.
Lando, H.A. et al, Journal Am Medical Women's Association, vol. 51(1–2), Jan–Apr. 1996, pp. 31–34.
Buchkremer, G. et al., Addictive Behaviors, vol. 14(2), 1989, pp. 229–238.
Müller, Ph. et al., Lung, vol. 168, 1990, pp. 445–453.
Miller, G.H. et al., The Journal of Family Practice, vol. 34(6), Jun. 1992, pp. 759–60, 762–776.
Campbell, I.A. et al., Respiratory Medicine, vol. 90(1), Jan. 1996, pp. 47–51.
Benowitz, N.L. et al., British Journal of Clinical Pharmacology, vol. 43(3), Mar. 1997, pp. 259–267.
Rose, J. E. et al. Clinical Pharmacology & Therapeutics, vol. 56(1), Jul. 1994, pp. 86–99.
Westman, E.C. et al., Archives of Internal Medicine, vol. 157(3), Feb. 10, 1997, pp. 335–40.
Pierce, J.P. et al., Journal of the National Cancer Institute, vol. 87(2), Jan. 18, 1995, pp. 87–93.
Paoletti, P. et al., European Respiratory Journal, vol. 9(4), Apr. 1996, pp. 643–51.
Ruiz Jimenez, C.A. et al., European Respiratory Journal, vol. 10(3), Mar. 1997, pp. 573–575.
Benowitz, N.L., "Cigarette Smoking and Nicotine Addition," Medical Clinics of North America, vol. 76, pp. 416–437, 1992.
Jorenby, D.E. et al., Psychopharmacology, vol. 128, 1996, pp. 130–138.
Bjornson–Benson, W. et al., Addictive Behaviors, vol. 18, 1993, pp. 491–502.
Lindley, C., Support Care Cancer, vol. 2, 1994, pp. 319–326.
Zevin, S. et al., Clinical Pharmacology & Therapeutics, vol. 64(1), Jul. 1998, pp. 87–95.
Dale, L.C. et al., JAMA, vol. 274(17), Nov. 1, 1996, pp. 1363–1368.
Fagerström, K.O. et al., Psychopharmacology, vol. 111, 1993, pp. 271–277.
Fredrickson, P.A. et al. Psychopharmacology, vol. 122, 1995, pp. 215–222.
Gourlay, S.G. et al., BMJ, vol. 311, Aug. 5, 1995, pp. 363–366.
Gupta, S.K. et al., J. Clin. Pharmacol., vol. 35, 1995, pp. 985–989.
Hurt, R.D. et al., JAMA, vol. 271(8), Feb. 23, 1994, pp. 595–600.
Jorenby, D.E. et al., JAMA, vol. 274(17), Nov. 1, 1995, pp. 257–262.
Kornitzer, M. et al., Preventive Medicine, vol. 24, 1995, pp. 41–47.
Lehmann, K.A. et al., Annals of Medicine, vol. 27, 1995, pp. 271–282.
Sachs, D.P. et al., Arch. Intern. Med., vol. 153, Aug. 23, 1993, pp. 1881–1890.
Sachs, D.P.L. et al., Eur. Respir. J. 1996, vol. 9, pp. 629–631.
Palmer, K.J. et al., Drugs, vol. 44(3), 1992, pp. 498–529.
Lifrak, P. et al., The American Journal on Addictions, vol.6(2), 1992, pp. 93–98.
Physicians' Desk Reference for Nonprescription Drugs, 19th Edition, 1998, pp. 776–780.
Physicians' Desk Reference, 52nd Edition, 1998, pp. 1813–1814.

* cited by examiner

*Primary Examiner*—Neil S. Levy
(74) *Attorney, Agent, or Firm*—John D. Thallemer

(57) ABSTRACT

The present invention is directed to patient-controlled, flexible-dosing methods of treatment utilizing transdermal nicotine patch devices, optionally with other nicotine delivery systems, to abate the use of tobacco in humans.

12 Claims, No Drawings

METHODS TO ABATE THE USE OF TOBACCO BY HUMANS

FIELD OF THE INVENTION

The present invention relates to methods of treatment to abate the use of tobacco by humans.

BACKGROUND OF THE INVENTION

Transdermal patches containing nicotine have been tested, approved and marketed as nicotine replacement products. Reported methods for using such transdermal patches typically utilize fixed, non-aggressive dosage regimens, some of which include tapering of the level of nicotine in the transdermal patches over the course of the treatment period. For example, the labeling of some products impose fixed tapering dosing schemes which utilize transdermal patches containing about 21 milligrams (mg) of total absorbable nicotine for 6 weeks, transdermal patches containing about 14 mg of total absorbable nicotine for 2 weeks, and transdermal patches containing about 7 mg of total absorbable nicotine for 2 weeks. Other reported methods utilize a fixed dosing scheme, i.e. there is no tapering of the amount of absorbable nicotine present in the transdermal patch. For instance, it has been reported to use transdermal patches containing about 15 mg of absorbable nicotine for 6 weeks.

Two published clinical studies compare quit rates for 22 mg and 44 mg patches. Neither study demonstrated a statistically significant difference in long term quit rates, though end of treatment success rates were significantly higher in those receiving the 44 mg dose. However, a sub-analysis suggested that in patients receiving minimal smoking cessation guidance, the 44 mg dose produced greater abstinence than did the 22 mg dose (68% vs. 45%, $p<0.01$) at the end of 4 weeks of treatment. Patients receiving individual or group counseling did not demonstrate this significant effect. Other studies suggest that smokers who use standard-dose nicotine patches as directed, who have few adverse effects, and who relapse because of persistent nicotine withdrawal symptoms or craving should be considered for dosages higher than 21 mg per day of standard patch therapy.

Two publications have reported higher quit rates when nicotine patches, used according to conventional teachings, were supplemented with nicotine gum.

There is consistent evidence from existing clinical trials that currently reported dosing schemes utilizing transdermal nicotine patches alone provides less than adequate nicotine replacement in most smokers. While it has been shown that at one year after initiation of reported nicotine treatment methods, successful quit rates are twice those of placebo, nevertheless, even with treatment by a general practitioner, less than 1 out of 4 attempts to cease using tobacco are successful in the first 2–3 months of a cessation attempt when reported methods of treatment are used.

Irregardless of which reported method is used, at the end of the conventional, pre-determined and fixed treatment period, there is no provision or consideration for those "treated" patients who either have exhausted the conventional treatment methods, yet still have the need to use tobacco products, or have failed to complete the conventional treatment methods due to their unabated need to use tobacco products. Accordingly, improved methods of treatment to eliminate or substantially reduce the need in humans to use tobacco are desirable.

SUMMARY OF THE INVENTION

The present invention is directed to a patient-controlled method of treatment to abate tobacco use in humans. The method comprises:

(a) upon commencement of treatment, i.e. Day 1 of treatment, applying to the skin of a human at least one transdermal nicotine patch device (TNPD) comprising a total absorbable dosage of nicotine (TAND) effective to abate symptoms associated with withdrawal from nicotine (NWS), the TAND not to exceed a maximum amount effective to induce symptoms associated with excess dosing of nicotine (NES), and the TAND to be determined by the human, (b) about 16 to about 24 hours after application of the TNPD applied in step (a), removing the TNPD applied in step (a) and applying to the skin of the human at least one TNPD comprising a TAND effective to abate the NWS, the TAND not to exceed a maximum amount effective to induce NES and the TAND to be determined by the human, (c) about 16 to about 24 hours after application of the TNPD applied in step (b), removing the TNPD applied in step (b) and applying to the skin of the human at least one TNPD comprising a TAND effective to abate the NWS, the TAND not to exceed a maximum amount effective to induce NES and the TAND to be determined by the human, (d) about 16 to about 24 hours after application of TNPD applied in step (c), removing the TNPD applied in step (c) and for a first continuous period of time, commencing upon the commencement of the treatment and extending about six weeks therefrom, and on an interval of about 24 hours, applying to the skin of the human at least one TNPD comprising a TAND effective to abate the NWS and removing the TNPD about 16 to about 24 hours after application thereof, the TAND not to exceed a maximum amount effective to induce NES and the TAND to be determined by the human, (e) upon completion of the first continuous period of time, applying to the skin of the human at least one TNPD comprising a TAND effective to abate the NWS, the TAND not to exceed a maximum amount effective to induce NES and the TAND to be determined by the human, (f) about 16 to about 24 hours after application of TNPD applied in step (e), removing the TNPD applied in step (e) and for a second continuous period of time, commencing upon commencement of step (e) and extending about two weeks therefrom, and on an interval of about 24 hours, applying to the skin of the human at least one TNPD comprising a TAND effective to abate the NWS and removing the TNPD about 16 to about 24 hours after application thereof, the TAND not to exceed a maximum amount effective to induce NES and the TAND to be determined by the human, (g) upon completion of the second continuous period of time, applying to the skin of the human at least one TNPD comprising a TAND effective to abate the NWS, the TAND not to exceed a maximum amount effective to induce NES and the TAND to be determined by the human, (h) about 16 to about 24 hours after application of TNPD applied in step (g), removing the TNPD applied in step (g) and for a third continuous period of time, commencing upon commencement of step (g) and extending about two weeks therefrom, and on an interval of about 24 hours, applying to the skin of the human at least one TNPD comprising a TAND effective to abate the NWS and removing the TNPD about 16 to about 24 hours after application thereof, the TAND not to exceed a maximum amount effective to induce NES and the TAND to be determined by the human, (i) upon completion of step (h), the human abstaining from use of any TNPD or tobacco for a fourth continuous period of time, commencing upon completion of the third continuous period of time and extending at least seven days therefrom; and (j) optionally, as determined by the human, for a fifth continuous period of time, commencing at least seven days after commencement of the fourth continuous period of time, but not more than a predetermined period of time, e.g. about 52 weeks from commencement of the treatment, and extending not less than about two weeks from commencement of the fifth continuous period of time, and on an interval of about 24 hours, applying to the skin of the human at least one TNPD containing a TAND effective to abate the NWS in the human and removing the TNPD about 16 to about 24 hours after application thereof, the TAND not to exceed a maximum amount effective to induce NES and the TAND to be determined by the human, until such time as the human abates tobacco use. In the present invention, the human adjusts the effective TAND based on the human's need to abate the NWS or to avoid or minimize the NES, and the necessity to exercise optional step (j) is determined by the human, based on criteria described herein. Should one determine that, in order to abate the NWS during treatment, one needs to revert back to a higher TAND, i.e. a rescue dosage, one may increase the TAND within the noted guidelines of treatment according to the severity of his/her particular NWS.

DETAILED DESCRIPTION OF THE INVENTION

TNPD is used interchangeably herein with "transdermal nicotine patch device", or "patch(es)", or "transdermal patch". TAND is used interchangeably herein with "total absorbable nicotine dose/dosage", or "total absorbable dose/dosage", or "dose/dosage". NWS is used interchangeably herein with "symptoms associated with nicotine withdrawal", or "nicotine withdrawal symptoms". NES is used interchangeably herein with "symptoms associated with excess dosing of absorbable nicotine", or "nicotine excess symptoms". The terms "patient" and "human" are used interchangeably herein.

Due to substantial interpatient variability of nicotine blood levels, it is unlikely that a single dose of nicotine replacement can be optimal for all humans. It is believed that the present invention will provide an acceptable risk/benefit in terms of adequate safety and provision of higher nicotine replacement doses to match better a human's personal needs in abating NWS. In view of the interpatient variability inherent in smoking, it is believed that the patient-controlled, flexible treatment of the present invention will eliminate entirely, or at least substantially reduce, use of tobacco in humans who undergo such treatment. Forms of such tobacco use are well known and include cigarettes, cigars and pipes, as well as "smokeless" tobacco products such as tobacco to be chewed or otherwise placed and kept in the mouth of humans.

The present invention provides at least three advantages over conventional tobacco/nicotine treatment methods. First, higher TAND is permitted in those humans who require higher levels of absorbed nicotine to abate NWS. By TAND, it is meant that amount of nicotine which is absorbed by the human and which reaches systemic circulation over a period of time of from about 16 to about 24 hours. The primary and required nicotine-delivery device used in the present invention is the TNPD. As such, nicotine is delivered transdermally via the TNPD.

When TNPD are the sole delivery devices used, the maximum TAND according to steps (a) through (d) is about 66 milligrams, the maximum TAND according to steps (e) and (f) is about 42 milligrams, the maximum TAND according to steps (g) and (h) is about 21 milligrams, and the maximum TAND according to step (j) is about 66 milligrams. It is noted that the numerical maximum TAND set forth herein are calculated based on nicotine typically absorbed via the skin by a TNPD. As discussed below, depending on the particular optional nicotine-delivery form chosen and the corresponding absorption by the human of nicotine provided by the form, the actual maximum TAND may vary, although the determining factor in recognizing when one is approaching the maximum TAND, that being the onset of NES, will be governed by the human's personal tolerance to nicotine, etc. Thus, based on factors such as the human's body weight, personal tolerance, etc., a broad range of daily dose exposure is likely to be observed in the treated population.

Second, "rescue" dosing of nicotine is permitted in the event that the human determines at some point during treatment that a temporary increase in nicotine levels is required in order to abate NWS prior to further reduction or elimination of nicotine during treatment. While the additional "rescue" nicotine may be delivered solely via the TNPD, other nicotine-delivery forms may be used to deliver additional nicotine for "rescue" purposes. Such additional forms include, but are not limited to, for example, nicotine gum, lozenges, or oral sprays, whereby nicotine is absorbed by the human via the buccal or sublingual route. The rescue nicotine also may be delivered via nasal sprays or inhalers, or other such devices which deliver nicotine to the lungs, whereby the nicotine is absorbed in the lungs. Again, the actual calculated maximum TAND may vary depending on factors of absorption via the different routes, such as skin, mucous membranes and the respiratory tract.

When TNPD is the sole device used for delivering nicotine, within any particular 16–24 hour period of time, or within any stage of treatment, one may increase the TAND from, for example, 22 mg to 44 or 66 mg in the case of step (d), or from 14 mg to 28 or 42 mg in the case of step (f). One also may repeat a particular stage of treatment, for example, by returning from steps (e) or (f) to step (d), or returning from step (g) or (h) to steps (e) or (f), and then continue treatment as described.

Third, long-term treatment is permitted for those who require longer periods of treatment than are provided for by conventional treatment methods. For example, the present invention provides for a pre-determined period of treatment which may last as long as, for example, up to one year after commencement of treatment, while conventional treatments last only for six to ten weeks.

The TAND used at various stages of treatment according to the present invention is not determined merely by a rigid regimen of decreasing nicotine levels which is pre-determined without consideration for the human's personal tobacco use, needs, or tolerance to NWS and NES. Rather, the present invention is patient-controlled, meaning that it is the patient who determines what TAND is required over the course of treatment, or at various stages of treatment, in order to abate his/her NWS or to avoid or minimize his/her NES.

The patient bases this determination in part on two criteria. One criterion used by the patient to determine the appropriate TAND is the patient's personal physical NWS or NES and tolerance thereto and his/her personal requirements to abate NWS or to avoid or minimize NES. For example, should the patient have a strong urge or craving to use tobacco products, this would be an indication to the patient that additional nicotine is required to abate the urge or craving. Should the patient experience any of the NES, this would be an indication to the patient that nicotine intake should be reduced to avoid these symptoms. In order to assess and to treat appropriately the personal physical symptoms with respect to proper TAND, the patient may refer to and/or rely on a behavioral support program which may include, for example, printed instructions and/or labels, or other oral instructions, advice or information given by qualified individuals who have been trained in giving advice on methods of treatment and appropriate TAND vis-à-vis NWS and NES. Additionally, the patient may consult with a health care provider as to what response to take with respect to experiencing NWS or NES. The point is that the patients themselves, once having the educational benefit and guidance of the behavioral support program and/or the health care provider, will be able to assess their own physical NWS and/or NES on a daily basis and to respond appropriately in adjusting the TAND accordingly.

NWS include, without limitation, irritability, restlessness, insomnia, drowsiness, difficulty concentrating (e.g. impaired task performance), anxiety, hunger and cravings, i.e. a strong urge for nicotine. The patient may either experience NWS on a continuous basis, or may experience breakthrough NWS, such as cravings, which may prompt the patient to utilize tobacco in absence of "rescue" dosing. NES include vomiting, diarrhea, cold sweat, blurred vision, difficulty hearing, mental confusion, weakness, and fainting.

The NWS and NES may range from mild, i.e. they are noticeable to the patient but do not require either a reduction or increase of TAND to abate such symptoms; to moderate, i.e. they do interfere with the patient's daily activities and possibly require an increase or reduction of TAND to abate such symptoms; to severe, i.e. they are intolerable to the patient and necessitate increasing or reducing the TAND to abate the symptoms. Particularly once the patient is counseled with respect to such symptoms prior to commencement of treatment, the NWS and NES are readily recognizable by the patient. Upon experiencing such symptoms, the patient will be able to determine, on a personal basis, what TAND is required at the particular point in treatment in order to abate NWS, so as to avoid or minimize tobacco use, or in order to avoid or reduce NES.

TNPD used according to the present invention are conventional and typically contain about 7, 11, 14, 21 or 22 milligrams of TAND per patch. Such TNPD are well known to those skilled in the art of treating nicotine/tobacco addiction. Commercially available TNPD include Habitrol®, available from Novartis Consumer Health, Inc, Nicoderm® CQ™, available from Smith Kline-Beecham, Prostep®, available from Elan Pharmaceuticals, and Nicotrol®, available from McNeil Consumer Consumer Products Company.

In addition to the commercial products noted, which presently contain only nicotine as the active ingredient for treating NWS, TNPD contemplated and claimed include those transdermal devices containing nicotine in combination with other active ingredients which may serve to enhance reduction of NWS or otherwise enhance the efficacy of the TNPD in treatment. For instance, pharmaceutically effective amounts of other central nervous system active agents, e.g. mecamylamine, physostigmine, clomipramine, ABT-418 (Abbott Laboratories), CMI 477 (CytoMed Company), GPI 2138 (Guilford Company), BW 1555U88 (Glaxo Wellcome), LY 354740 (Lilly Pharmaceutical), lesoptron, buproprion, chlorisondamine, carbamoyol, oxamine, lobeline, and olazapine, may be employed. Pharmaceutically effective amounts of metabolic enhancers, e.g. barbiturates, metabolic inhibitors, e.g. cimetidine, or nicotine metabolites, e.g. cotinine or metanicotine, or other alkaloids may be employed. Other classes of additional active agents include immunologics, e.g. nicotine vaccine or nicotine plus protein carrier, topical oral mucousa active agents, e.g. citric acid, and herbals, e.g. St. John's Wort.

Upon commencement of treatment, the patient will apply at least one TNPD comprising a TAND of at least about 21 mg. Conveniently, treatment will start on the morning of the first day and, accordingly, the TNPD will be applied in the morning. While, for practical purposes, one 21 mg TNPD may be used, any combination of TNPD which comprise a TAND of about 21 mg may be used. While it is preferred to limit the TAND to about 21 mg on the first day of treatment, should the patient determine that 21 mg TAND is not effective to control the patient's NWS, the patient may elect to apply additional TNPD until such time as the patient's NWS have been abated, i.e., the patient has refrained from using tobacco, provided that the TAND does not exceed about 66 mg in Day 1. The TNPD is to be removed about 16 to about 24 hours after application thereof, preferably the following morning. Application sites should be rotated to prevent application site reactions.

Not more than about 24 hours after application of the TNPD and subsequent to removal thereof (i.e. Day 2), the patient again will apply at least one TNPD comprising a TAND of at least about 21 mg. If the patient determines that 21 mg is not effective to abate his/her symptoms, the patient may add additional TNPD anytime during Day 2, provided that the TAND does not exceed about 66 mg in Day 2. Preferably, the TAND will not exceed about 44 mg on Day 2. Again, the TNPD will be removed approximately 16 to 24 hours after application thereof so that additional TNPD may be applied the following day.

After the patient has worn at least one TNPD comprising a TAND of about 42 mg on a given day, if the patient determines that additional nicotine is required to abate his/her NWS, the patient may increase the TAND to a maximum of about 66 mg in one day. In order to prevent under-dosing, and only if the patient continues to experience NWS, the patient should be encouraged to progress to a TAND of about 66 mg by Day 3 of treatment.

The patient must remain on a minimum TAND of at least about 21 mg nicotine per day for a first continuous time period commencing with the start of treatment (i.e. Day 1 of treatment) and extending 6 weeks therefrom. At anytime after the initial 6 weeks continuous period, if the patient determines that a 21 mg TAND is not required to abate the patient's NWS, the behavioral support program and/or a health care provider may suggest or advise a TAND of about 14 mg.

Upon completion of the first continuous time period, the patient will begin the following morning with at least one TNPD comprising a TAND of about 14 mg. Should the patient determine that 14 mg TAND is not sufficient to abate his/her NWS, the patient may rescue, i.e. use additional TNPD in order to avoid use of tobacco, provided that the TAND does not exceed about 42 mg per day.

While it is preferred that the patient use no more than three 14 mg patches per day subsequent to completion of the first continuous time period, nevertheless, if the patient determines that a higher TAND is needed to abate the NWS, the patient may return to the 21 mg patch and use as many as three per day until the patient is ready to try a lower TAND again. Irregardless of whether or not the patient remains on the 14–42 mg TAND regimen or rescues with a 21–66 mg TAND regimen, prior to continuing to the next stage of treatment, the patient must remain on a TAND of at least 14 mg per day for at least 2 weeks.

If at any time after completing 2 weeks on at least 14 mg TAND per day, the patient determines that a 14 mg TAND is not needed, the behavioral support program and/or the health care provider may suggest or advise use of the 7 mg patches. The patient will begin the following morning with one 7 mg patch. The patient may rescue with a second or a third 7 mg patch the same day if determined by the patient to be necessary.

While it is preferred that the patient use no more than three 7 mg patches per day subsequent to completing two weeks on at least 14 mg TAND per day, nevertheless, if the patient determines that a higher TAND is needed to abate the NWS, the patient may return to the 14 mg patch and use as many as three per day until ready to try a lower TAND again. Irregardless of whether or not the patient remains on the 7–21 mg TAND regimen or rescues with a 14–42 mg TAND regimen, prior to continuing to the next stage of treatment, patients should remain on at least one 7 mg patch per day for at least 2 weeks.

If at any time after 2 weeks on at least one 7 mg patch per day the patient determines that a 7 mg TAND is not needed, the behavioral support program and/or the health care provider may suggest or advise that the patient discontinue the use of all patches.

Those who successfully cease the use of tobacco products and who no longer use the patch will be discharged from treatment with 21 mg and 14 mg patches for rescue purposes. The patients may re-initiate TNPD use at anytime during the predetermined time period, e.g. one year from commencement of treatment, should they determine that this is required in order to abate NWS. In this way, should successful quitters feel the need to use tobacco during the predetermined time period, they may elect, instead, to re-initiate treatment with the TNPD. However, patients will be encouraged to have titrated downward and to be using one 7 mg patch (if any) per day for the 7 days prior to the end of the predetermined period of time, e.g. Week 52 after commencement of treatment.

As general treatment guidelines, but subject to the foregoing description, a typical patient dosing schedule according to the present invention would include 6 weeks on at least one 21 mg TAND patch per day, followed by 2 weeks on at least one 14 mg TAND patch per day, followed by 2 weeks on at least one 7 mg TAND patch per day.

A minimum of one patch should be applied every morning, with additional patches being added anytime throughout the day (except during the initiation period). The initiation period, i.e. the initial increase from 21 mg TAND per day to 63 mg TAND per day, preferably is implemented in a stepwise manner, e.g. 21 mg TAND on Day 1, 42 mg TAND on Day 2, 63 mg TAND on Day 3. However, after a patient has experienced and can tolerate the 63 mg-TAND per-day, the patient can dose freely with from one to three patches per day of any strength patch in order to abate the NWS.

If a patient complains of experiencing sleep disturbances (including nightmares), the behavioral support program and/or the health care provider may suggest or advise that the patient remove one or more patches at bedtime.

Any patient who feels the need to re-initiate patch use should be off the patch for at least 7 days and should re-initiate per the following guidelines. If the patient is smoking more than 10 cigarettes per day, the patient should re-initiate with one 21 mg TAND patch per day (titrated up to three 21 mg TAND patches per day), if necessary, for a minimum of 6 weeks. If the patient is smoking less than 10 cigarettes per day, the patient should re-initiate with one 14 mg TAND patch per day (titrated up to three 14 mg TAND patches per day), if necessary, for a minimum of 2 weeks. If a patient is still smoking after 7 weeks of treatment, the behavioral support program and/or the health care provider may suggest or advise that the patient stop smoking immediately or to discontinue treatment.

What is claimed is:

1. A patient-controlled method of treatment to abate tobacco use in humans, said method comprising:

(a) applying to the skin of a human at least one transdermal nicotine patch device comprising a total absorbable nicotine dose to be determined by the human which is effective to abate nicotine withdrawal symptoms, wherein the total absorbable nicotine dose does not exceed about 66 mg and does not induce nicotine excess symptoms;

(b) about 16 to about 24 hours after application of the transdermal nicotine patch device in Step (a), removing the transdermal nicotine patch device applied in Step (a) and applying to the skin of the human at least one transdermal nicotine patch device comprising a total absorbable nicotine dose to be determined by the human which is effective to abate nicotine withdrawal symptoms, wherein the total absorbable nicotine dose does not exceed about 66 mg and does not induce nicotine excess symptoms, provided that the total absorbable nicotine dose in Step (b) is greater than the total absorbable nicotine dose in Step (a);

(c) about 16 to about 24 hours after application of the transdermal nicotine patch device in Step (b), removing the transdermal nicotine patch device applied in Step (b) and applying to the skin of the human at least one transdermal nicotine patch device comprising a total absorbable nicotine dose to be determined by the human which is effective to abate nicotine withdrawal symptoms, wherein the total absorbable nicotine dose does not exceed about 66 mg and does not induce nicotine excess symptoms, provided that the total absorbable nicotine dose in Step (c) is greater than the total absorbable nicotine dose in Step (b);

(d) about 16 to about 24 hours after application of the transdermal nicotine patch device in Step (c), removing the transdermal nicotine patch device applied in Step (c) and for a first continuous period of time, beginning with the commencement of treatment and continuing for about six weeks therefrom, applying to the skin of the human at an interval of about 24 hours at least one transdermal nicotine patch device comprising a total absorbable nicotine dose to be determined by the human which is effective to abate nicotine withdrawal symptoms, wherein the total absorbable nicotine dose does not exceed about 66 mg and does not induce nicotine excess symptoms, and removing the transdermal nicotine patch device about 16 to about 24 hours after application thereof, provided that the total absorbable nicotine dose in Step (d) is less than or equal to the total absorbable nicotine dose in Step (c);

(e) after completion of the first continuous period of time, applying to the skin of the human at least one transdermal nicotine patch device comprising a total absorbable nicotine dose to be determined by the human which is effective to abate nicotine withdrawal symptoms, wherein the total absorbable nicotine dose does not exceed about 42 mg and does not induce nicotine excess symptoms;

(f) about 16 to about 24 hours after application of the transdermal nicotine patch device in Step (e), removing the transdermal nicotine patch device applied in Step (e) and for a second continuous period of time, beginning with the application in Step (e) and continuing for about two weeks therefrom, applying to the skin of the human at an interval of about 24 hours at least one transdermal nicotine patch device comprising a total absorbable nicotine dose to be determined by the human which is effective to abate nicotine withdrawal symptoms, wherein the total absorbable nicotine dose does not exceed about 42 mg and does not induce nicotine excess symptoms, and removing the transdermal nicotine patch device about 16 to about 24 hours after application thereof;

(g) after completion of the second continuous period of time, applying to the skin of the human at least one transdermal nicotine patch device comprising a total absorbable nicotine dose to be determined by the human which is effective to abate nicotine withdrawal symptoms, wherein the total absorbable nicotine dose does not exceed about 21 mg and does not induce nicotine excess symptoms;

(h) about 16 to about 24 hours after application of the transdermal nicotine patch device in Step (g), removing the transdermal nicotine patch device applied in Step (g) and for a third continuous period of time, beginning with the application in Step (g) and continuing for about two weeks therefrom, applying to the skin of the human at an interval of about 24 hours at least one transdermal nicotine patch device comprising a total absorbable nicotine dose to be determined by the human which is effective to abate nicotine withdrawal symptoms, wherein the total absorbable nicotine dose does not exceed about 21 mg and does not induce nicotine excess symptoms, and removing the transdermal nicotine patch device about 16 to about 24 hours after application thereof; and (i) after completion of the third continuous period of time, the human abstains from using any transdermal nicotine patch device or tobacco for at least seven days, provided that in at least one of Steps (b)–(h), the total absorbable nicotine dose is greater than the total absorbable nicotine dose in the prior step.

2. The method of treatment according to claim 1 which comprises, after completion of Step (i), applying to the skin of the human at an interval of about 24 hours at least one transdermal nicotine patch device comprising a total absorbable nicotine dose to be determined by the human which is effective to abate nicotine withdrawal symptoms, wherein the total absorbable nicotine dose does not induce nicotine excess symptoms, and removing the transdermal nicotine patch device about 16 to about 24 hours after application thereof, until such time as the human abates tobacco use.

3. The method of treatment according to claim 1 wherein the total absorbable nicotine dose in Step (a) is about 21 mg.

4. The method of treatment according to claim 3 wherein the total absorbable nicotine dose in Step (b) is about 42 mg.

5. The method of treatment according to claim 4 wherein the total absorbable nicotine dose in Step (c) is about 63 mg.

6. The method of treatment according to claim 5 wherein the total absorbable nicotine dose in Step (d) is from about 21 mg to about 63 mg.

7. The method of treatment according to claim 6 wherein the total absorbable nicotine dose in Step (e) is about 14 mg.

8. The method of treatment according to claim 7 wherein the total absorbable nicotine dose in Step (f) is from about 14 mg to about 42 mg.

9. The method of treatment according to claim 8 wherein the total absorbable nicotine dose in Step (g) is about 7 mg.

10. The method of treatment according to claim 9 wherein the total absorbable nicotine dose in Step (h) is from about 7 mg to about 21 mg.

11. The method of treatment according to claim 2 wherein the total absorbable nicotine dose is from about 7 mg to about 63 mg.

12. A patient-controlled method of treatment to abate tobacco use in humans, said method comprising:

(a) applying to the skin of a human at least one transdermal nicotine patch device comprising a total absorbable nicotine dose of about 21 mg;

(b) about 16 to about 24 hours after application of the transdermal nicotine patch device in Step (a), removing the transdermal nicotine patch device applied in Step (a) and applying to the skin of the human at least one transdermal nicotine patch device comprising a total absorbable nicotine dose of from about 21 mg to about 42 mg, provided that the total absorbable nicotine dose in Step (b) is greater than the total absorbable nicotine dose in Step (a);

(c) about 16 to about 24 hours after application of the transdermal nicotine patch device in Step (b), removing the transdermal nicotine patch device applied in Step (b) and applying to the skin of the human at least one transdermal nicotine patch device comprising a total absorbable nicotine dose of from about 21 mg to about 63 mg, provided that the total absorbable nicotine dose in Step (c) is greater than the total absorbable nicotine dose in Step (b;

(d) about 16 to about 24 hours after application of the transdermal nicotine patch device in Step (c), removing the transdermal nicotine patch device applied in Step (c) and for a first continuous period of time, beginning with the commencement of treatment and continuing for about six weeks therefrom, applying to the skin of the human at an interval of about 24 hours at least one transdermal nicotine patch device comprising a total absorbable nicotine dose of from about 21 mg to about 63 mg, and removing the transdermal nicotine patch device about 16 to about 24 hours after application thereof, provided that the total absorbable nicotine dose in Step (d) is less than or equal to the total absorbable nicotine dose in Step (c);

(e) after completion of the first continuous period of time, applying to the skin of the human at least one transdermal nicotine patch device comprising a total absorbable nicotine dose of from about 14 mg to about 42 mg;

(f) about 16 to about 24 hours after application of the transdermal nicotine patch device in Step (e), removing the transdermal nicotine patch device applied in Step (e) and for a second continuous period of time, beginning with the application in Step (e) and continuing for about two weeks therefrom, applying to the skin of the human at an interval of about 24 hours at least one transdermal nicotine patch device comprising a total absorbable nicotine dose of from about 14 mg to about 42 mg, and removing the transdermal nicotine patch device about 16 to about 24 hours after application thereof;

(g) after completion of the second continuous period of time, applying to the skin of the human at least one transdermal nicotine patch device comprising a total absorbable nicotine dose of from 7 mg to about 21 mg;

(h) about 16 to about 24 hours after application of the transdermal nicotine patch device in Step (g), removing the transdermal nicotine patch device applied in Step (g) and for a third continuous period of time, beginning with the application in Step (g) and continuing for about two weeks therefrom, applying to the skin of the human at an interval of about 24 hours at least one transdermal nicotine patch device comprising a total absorbable nicotine dose of from 7 mg to about 21 mg, and removing the transdermal nicotine patch device about 16 to about 24 hours after application thereof; and (i) after completion of the third continuous period of time, the human abstains from using any transdermal nicotine patch device or tobacco for at least seven days, provided that in at least one of Steps (b)–(h), the total absorbable nicotine dose is greater than the total absorbable nicotine dose in the prior step.

* * * * *